(12) United States Patent
Fukuda

(10) Patent No.: US 11,938,207 B2
(45) Date of Patent: Mar. 26, 2024

(54) COSMETIC COMPOSITION FOR SKIN

(71) Applicant: KAO CORPORATION, Tokyo (JP)

(72) Inventor: Teruyuki Fukuda, Wakayama (JP)

(73) Assignee: KAO CORPORATION, Tokyo (JP)

( * ) Notice: Subject to any disclaimer, the term of this patent is extended or adjusted under 35 U.S.C. 154(b) by 365 days.

(21) Appl. No.: 17/299,914

(22) PCT Filed: Nov. 22, 2019

(86) PCT No.: PCT/JP2019/045888
§ 371 (c)(1),
(2) Date: Jun. 4, 2021

(87) PCT Pub. No.: WO2020/116217
PCT Pub. Date: Jun. 11, 2020

(65) Prior Publication Data
US 2022/0031587 A1    Feb. 3, 2022

(30) Foreign Application Priority Data

Dec. 7, 2018  (JP) ................................ 2018-230174

(51) Int. Cl.
| | | |
|---|---|---|
| *A61K 8/34* | (2006.01) | |
| *A61K 8/25* | (2006.01) | |
| *A61K 8/31* | (2006.01) | |
| *A61K 8/42* | (2006.01) | |
| *A61K 8/81* | (2006.01) | |
| *A61K 8/898* | (2006.01) | |
| *A61Q 1/02* | (2006.01) | |

(52) U.S. Cl.
CPC ............. *A61K 8/34* (2013.01); *A61K 8/25* (2013.01); *A61K 8/31* (2013.01); *A61K 8/42* (2013.01); *A61K 8/8158* (2013.01); *A61K 8/817* (2013.01); *A61K 8/898* (2013.01); *A61Q 1/02* (2013.01); *A61K 2800/43* (2013.01); *A61K 2800/5424* (2013.01); *A61K 2800/5426* (2013.01); *A61K 2800/594* (2013.01)

(58) Field of Classification Search
CPC ...................................................... A61K 8/34
See application file for complete search history.

(56) References Cited

U.S. PATENT DOCUMENTS

| | | |
|---|---|---|
| 6,214,319 B1 | 4/2001 | Franzke et al. |
| 2013/0079368 A1 | 3/2013 | Omura et al. |
| 2014/0212363 A1 | 7/2014 | Harman et al. |
| 2014/0364394 A1 | 12/2014 | Tamura et al. |
| 2016/0051028 A1 | 2/2016 | Lahousse et al. |
| 2018/0028430 A1 | 2/2018 | Aoshima et al. |
| 2021/0085592 A1 | 3/2021 | Nagai et al. |

FOREIGN PATENT DOCUMENTS

| | | |
|---|---|---|
| CN | 107638307 A | 1/2018 |
| EP | 0 841 060 A2 | 5/1998 |
| JP | 10-130302 A | 5/1998 |
| JP | 11-12303 A | 1/1999 |
| JP | 11-80201 A | 3/1999 |
| JP | 2001-259517 A | 9/2001 |
| JP | 2007-99785 A | 4/2007 |
| JP | 2010-111625 A | 5/2010 |
| JP | 2013-40162 A | 2/2013 |
| JP | 2013-151660 A | 8/2013 |
| JP | 2015-520120 A | 7/2015 |
| JP | 2016-519094 A | 6/2016 |
| JP | 2016-121137 A | 7/2016 |
| JP | 2016-160205 A | 9/2016 |
| JP | 2017-39669 A | 2/2017 |
| JP | 2017-122076 A | 7/2017 |
| WO | WO 2013/036878 A1 | 3/2013 |
| WO | WO 2017/110979 A1 | 6/2017 |
| WO | WO 2019/044327 A1 | 3/2019 |

OTHER PUBLICATIONS

Extended European Search Report dated Aug. 9, 2022 in European Patent Application No. 19891731.2, 12 pages.
International Search Report dated Feb. 4, 2020 in PCT/JP2019/045888 filed on Nov. 22, 2019, 3 pages.

*Primary Examiner* — Benjamin J Packard
(74) *Attorney, Agent, or Firm* — Oblon, McClelland, Maier & Neustadt, L.L.P.

(57) ABSTRACT

ABSTRACT A cosmetic composition for skin containing a solvent A, a solvent B, and a polymer C, where a boiling point of the solvent A is lower than 99° C., and a distance Ra of the Hansen solubility parameter of the solvent A to water is 36 or less; a boiling point of the solvent B is 150° C. or higher, and a distance Ra of the Hansen solubility parameter of the solvent B to water is 40 or more; and the solvent B is compatible with the solvent A, and the polymer C is soluble in the solvent A but insoluble in the solvent B. A cosmetic coating film for skin includes the cosmetic composition.

20 Claims, No Drawings

COSMETIC COMPOSITION FOR SKIN

FIELD OF THE INVENTION

The present invention relates to a cosmetic composition for skin and a cosmetic coating film for skin.

BACKGROUND OF THE INVENTION

Conventionally, in order to cover the skin dullness or improve the brightness of coating finish, skin cosmetics, such as a makeup cosmetic, have been blended with an inorganic pigment with a high concealing power, such as titanium oxide, zinc oxide, and iron oxide.

For example, JP 2016-121137 A (PTL 1) describes a cosmetic containing titanium oxide having an average particle diameter of 0.2 μm or more and resin fine particles having an average particle diameter of 0.01 to 100 μm for the purpose of providing a cosmetic capable of giving high whiteness or concealing power.

In addition, JP 2015-520120 A (PTL 2) describes a cosmetic composition containing a plate type filler having predetermined refractive index and particle diameter, a silicone elastomer, and a filler having an oil absorption capacity of 1 mL/g or more in a physiologically acceptable medium for the purpose of long lasting an effect for hiding the skin imperfections or the like.

SUMMARY OF THE INVENTION

The present invention relates to the following [1].
[1] A cosmetic composition for skin containing a solvent A, a solvent B, and a polymer C, wherein
a boiling point of the solvent A is lower than 99° C., and a distance Ra of the Hansen solubility parameter of the solvent A to water as expressed by the following equation (1) is 36 or less,
a boiling point of the solvent B is 150° C. or higher, and a distance Ra of the Hansen solubility parameter of the solvent B to water as expressed by the following equation (1) is 40 or more, and
the solvent B is compatible with the solvent A, and the polymer C is soluble in the solvent A but insoluble in the solvent B:

$$Ra = (4 \times \Delta D^2 + \Delta P^2 + \Delta H^2)^{0.5} \tag{1}$$

wherein,
ΔD is a difference of dispersing component in the Hansen solubility parameter between a solvent and water,
ΔP is a difference of polar component in the Hansen solubility parameter between a solvent and water, and
ΔH is a difference of hydrogen-binding component in the Hansen solubility parameter between a solvent and water.

DETAILED DESCRIPTION OF THE INVENTION

According to the technologies of PTLs 1 and 2, the whiteness is expressed by blending with an inorganic pigment having a high refractive index. However, in recent years, with respect to zinc oxide and titanium oxide, the restrictions on use are becoming severe due to various laws and regulations. For that reason, the development of cosmetic compositions for skin which have a high whiteness and are excellent in concealment even without using an inorganic pigment is desired.

The present invention relates to a cosmetic composition for skin which has a high whiteness and is excellent in concealment even without using an inorganic pigment and a cosmetic coating film for skin.

The present inventor has found that in a composition containing two kinds of solvents each having a predetermined boiling point and a polymer, by setting the Hansen solubility parameters of these two kinds of solvents to water to a prescribed range, respectively and allowing the compatibilities of the two kinds of solvents and the solubility of the polymer in each of the solvents to fall in a specified relation, respectively, the composition has a high whiteness and improved concealment even without using an inorganic pigment.

Specifically, the present invention relates to the following [1] and [2].
[1] A cosmetic composition for skin containing a solvent A, a solvent B, and a polymer C, wherein
a boiling point of the solvent A is lower than 99° C., and a distance Ra of the Hansen solubility parameter of the solvent A to water as expressed by the following equation (1) is 36 or less,
a boiling point of the solvent B is 150° C. or higher, and a distance Ra of the Hansen solubility parameter of the solvent B to water as expressed by the following equation (1) is 40 or more, and
the solvent B is compatible with the solvent A, and the polymer C is soluble in the solvent A but insoluble in the solvent B:

$$Ra = (4 \times \Delta D^2 + \Delta P^2 + \Delta H^2)^{0.5} \tag{1}$$

wherein,
ΔD is a difference of dispersing component in the Hansen solubility parameter between a solvent and water,
ΔP is a difference of polar component in the Hansen solubility parameter between a solvent and water, and
ΔH is a difference of hydrogen-binding component in the Hansen solubility parameter between a solvent and water.
[2] A cosmetic coating film for skin, which is formed from the cosmetic composition for skin as set forth above in [1].

In accordance with the present invention, it is possible to provide a cosmetic composition for skin which has a high whiteness and is excellent in concealment even without using an inorganic pigment and a cosmetic coating film for skin.

[Cosmetic Composition for Skin]

The cosmetic composition for skin of the present invention (hereinafter also referred to as "cosmetic composition") is a cosmetic composition containing a solvent A, a solvent B, and a polymer C, wherein a boiling point of the solvent A is lower than 99° C., and a distance Ra of the Hansen solubility parameter of the solvent A to water as expressed by the following equation (1) is 36 or less; a boiling point of the solvent B is 150° C. or higher, and a distance Ra of the Hansen solubility parameter of the solvent B to water as expressed by the following equation (1) is 40 or more; and the solvent B is compatible with the solvent A, and the polymer C is soluble in the solvent A but insoluble in the solvent B:

$$Ra = (4 \times \Delta D^2 + \Delta P^2 + \Delta H^2)^{0.5} \tag{1}$$

wherein,
ΔD is a difference of dispersing component in the Hansen solubility parameter between a solvent and water,
ΔP is a difference of polar component in the Hansen solubility parameter between a solvent and water, and ΔH is a difference of hydrogen-binding component in the Hansen solubility parameter between a solvent and water.

In the present invention, the wording "compatible" refers to a phenomenon in which in a mixed system containing the solvent A and the solvent B, the solvent A and the solvent B are mutually dissolved. The case where when the solvent A and the solvent B are mixed and allowed to stand, they are not separated in multiple phases, or the case where when the solvent A and the solvent B are mixed and subjected to a stirring operation, no phase separation is caused, so that they do not become cloudy, is judged such that the solvent A and the solvent B are in a compatibilized state with each other.

The polymer C is one which is soluble in the solvent A but insoluble in the solvent B and is dissolved in the cosmetic composition.

In the present invention, the wording "the polymer C is soluble in the solvent A" means that the dissolved amount when the polymer C after drying at 105° C. for 2 hours and reaching a constant weight is dissolved in 100 g of the solvent A at 25° C. is 5 g or more. The aforementioned dissolve amount is preferably 10 g or more from the viewpoint of improving the whiteness and the concealment.

In the present invention, the wording "the polymer C is insoluble in the solvent B" means that the dissolved amount when the polymer C after drying at 105° C. for 2 hours and reaching a constant weight is dissolved in 100 g of the solvent B at 25° C. until it is saturated is less than 5 g. The foregoing dissolved amount is preferably 2 g or less from the viewpoint of improving the whiteness and the concealment.

The judgement regarding "compatible" or "soluble" is performed at 25° C.

In the present invention, the "Hansen solubility parameter" is expressed by dividing the solubility parameter (SP value) introduced by Hildebrand into three components (dispersing component D, polar component P, and hydrogen-binding component H). The D, P, and H of the respective solvents are described in detail in "HANSEN SOLUBILITY PARAMETERS" A User's Handbook Second Edition. In addition, the HSP values regarding a lot of solvents and resins are also described in Wesley L. Archer, "Industrial Solvents Handbook" and the like.

The D, P, and H of the respective solvents can also be determined using a software HSPiP of Charles Hansen Consulting, Inc. (Horsholm, Denmark, hansen-solubility-.com).

In the present invention, with respect to solvents registered in the database of HSPiP Version 4.1.03 (see the literatures of various HSP's), the values are adopted, and with respect to solvents not registered in the database, values estimated from the aforementioned HSPiP are adopted.

In accordance with the present invention, it is possible to provide a cosmetic composition which has a high whiteness and is excellent in concealment even without using an inorganic pigment. Although the reason for this is not elucidated yet, the following may be considered.

The cosmetic composition of the present invention contains the solvent A and the solvent B which are different from each other with respect to the boiling point and the distance Ra of the Hansen solubility parameter to water and the polymer C which is soluble in the solvent A but insoluble in the solvent B.

When such a cosmetic composition is coated on the skin, the heat of vaporization is deprived due to volatilization of the solvent A in the coating film, and the moisture in the air is condensed on the surface of the coating film and attached as fine waterdrops. In the present invention, the solubility parameters to water of the solvent A and the solvent B fall within the specified ranges, respectively, and therefore, the solvent B having been compatibilized with the solvent A causes phase separation due to this attachment of water. Then, it may be considered that since the polymer C is soluble in the solvent A but insoluble in the solvent B, the polymer C coats the phase-separated solvent B, and coalescence of the solvent B is suppressed, whereby primary particles having a core-shell structure in which the solvent B constitutes the core, and the polymer C constitutes the shell are formed. Furthermore, it may be considered that following the volatilization of the solvent A and the surface alignment of the formed primary particles, a cell-shaped convection structure regularly divided within the coating film, so-called "Benard cells", is generated, the primary particles are accumulated due to the Benard convection in each cell to form secondary particles, whereby the cosmetic coating film is obtained. As a result, it may be conjectured that the light is scattered due to the particle structure formed within the cosmetic coating film, the high whiteness is expressed, and the concealment is improved.

<Solvent A>

The cosmetic composition of the present invention contains the solvent A.

As for the solvent A, its boiling point is lower than 99° C., and the distance Ra of the Hansen solubility parameter of the solvent A to water as expressed by the aforementioned equation (1) is 36 or less. Furthermore, the solvent A is compatible with the solvent B and dissolves the polymer C therein. According to this, on the occasion of coating the cosmetic composition on the skin, the heat of vaporization is deprived following volatilization of the solvent A, fine waterdrops attach onto the surface of the coating film, thereby enabling one to cause phase separation between the solvent A and the solvent B.

The boiling point of the solvent A is lower than 99° C., preferably 98° C. or lower, more preferably 90° C. or lower, and still more preferably 80° C. or lower from the viewpoint of forming the primary particles and improving the whiteness and the concealment, and is also preferably 50° C. or higher, more preferably 60° C. or higher, and still more preferably 70° C. or higher from the viewpoint of handling properties.

The distance Ra of the Hansen solubility parameter of the solvent A to water is 36 or less, preferably 32 or less, more preferably 30 or less, still more preferably 28 or less, and yet still more preferably 26 or less, and is also preferably 10 or more, more preferably 15 or more, still more preferably 20 or more, and yet still more preferably 22 or more, from the viewpoint of forming the primary particles and improving the whiteness and the concealment.

The solvent A may be used alone or in combination of two or more thereof. In the case of using the solvent A in combination of two or more thereof, the boiling point of the solvent A and the distance Ra of the Hansen solubility parameter of the solvent A to water can be determined as a weighted average value resulting through weighing in terms of the content (% by mass) of each of the solvents.

The solvent A is preferably a monohydric alcohol having 1 or more and 4 or less carbon atoms, and examples thereof include ethanol, propanol, isopropanol, and tert-butyl alcohol. Above all, from the viewpoint of improving the whiteness and the concealment, preferred is at least one selected from the group consisting of ethanol propanol, isopropanol, and tert-butyl alcohol, and more preferred is ethanol.

<Solvent B>

The cosmetic composition of the present invention contains the solvent B.

As for the solvent B, its boiling point is 150° C. or higher, and the distance Ra of the Hansen solubility parameter of the solvent B to water as expressed by the aforementioned equation (1) is 40 or more. Furthermore, the solvent B is compatible with the solvent A and does not dissolve the polymer C therein. According to this, on the occasion when fine waterdrops attach onto the surface of the coating film due to volatilization of the solvent A, phase separation between the solvent A and the solvent B is caused, and the primary particles in which the solvent B is coated with the polymer C are formed.

The boiling point of the solvent B is 150° C. or higher, preferably 155° C. or higher, more preferably 160° C. or higher, still more preferably 165° C. or higher, and yet still more preferably 170° C. or higher from the viewpoint of forming the primary particles and improving the whiteness and the concealment, and is also preferably 300° C. or lower, more preferably 270° C. or lower, still more preferably 250° C. or lower, yet still more preferably 230° C. or lower, even yet still more preferably 210° C. or lower, and even still more preferably 180° C. or lower from the viewpoint of handling properties.

The distance Ra of the Hansen solubility parameter of the solvent B to water is 40 or more, preferably 42 or more, and more preferably 44 or more, and is also preferably 60 or less, more preferably 57 or less, and still more preferably 55 or less, from the viewpoint of forming the primary particles and improving the whiteness and the concealment.

The solvent B may be used alone or in combination of two or more thereof. In the case of using the solvent B in combination of two or more thereof, the boiling point of the solvent B and the distance Ra of the Hansen solubility parameter of the solvent B to water can be determined as a weighted average value resulting through weighing in terms of the content (% by mass) of each of the solvents.

From the viewpoint of improving the whiteness and the concealment, the solvent B preferably contains at least one selected from the group consisting of a hydrocarbon oil and a silicone oil.

Examples of the hydrocarbon oil include α-olefin oligomers, liquid paraffins, liquid isoparaffins, such as isododecane, isohexadecane and hydrogenated polyisobutene, heavy liquid isoparaffins, liquid ozokerite, squalane, pristane, and squalene. The hydrocarbon oil is preferably a liquid isoparaffin, and more preferably at least one selected from the group consisting of isododecane and hydrogenated polyisobutene.

A weight average molecular weight of the hydrocarbon oil is preferably 150 or more, and more preferably 160 or more, and is also preferably 1,000 or less, more preferably 500 or less, and still more preferably 300 or less.

A viscosity at 20° C. of the hydrogenated polyisobutene is preferably 0.5 mPa·s or more, more preferably 0.7 mPa·s or more, and still more preferably 1 mPa·s or more, and is also preferably 30 mPa·s or less, more preferably 25 mPa·s or less, and still more preferably 20 mPa·s or less. The viscosity at 20° C. of the hydrogenated polyisobutene can be measured with an E-type viscometer by the method described in the section of Examples.

Examples of the silicone oil include linear silicone oils, such as trisiloxane; branched silicone oils, such as methyltrimethicone; and cyclic silicone oils, such as methylcyclopolysiloxane. Above all, preferred are trisiloxane and methyltrimethicone.

A weight average molecular weight of the silicone oil is preferably 150 or more, and more preferably 160 or more, and is also preferably 1,000 or less, more preferably 500 or less, and still more preferably 300 or less.

A viscosity at 25° C. of the silicone oil is preferably 0.5 mPa·s or more, and is also preferably 20 mPa·s or less, more preferably 10 mPa·s or less, still more preferably 5 mPa·s or less, and yet still more preferably 3 mPa·s or less. The viscosity at 25° C. of the silicone oil can be measured with an E-type viscometer by the method described in the section of Examples.

The solvent B may also be one containing, in addition to the hydrocarbon oil or the silicone oil, an additive, such as a moisturizer, an ultraviolet absorber, a pest repellent, a wrinkling-preventing agent, a fragrance, and a dye.

In the case where the solvent B contains at least one selected from the group consisting of a hydrocarbon oil and a silicone oil each having a weight average molecular weight of 150 or more and 1,000 or less, the content of at least one selected from the group consisting of a hydrocarbon oil and a silicone oil each having a weight average molecular weight of 150 or more and 1,000 or less in the solvent B is preferably 50% by mass or more, more preferably 70% by mass or more, and still more preferably 90% by mass or more from the viewpoint of improving the whiteness and the concealment.

<Polymer C>

In the present invention, the polymer C coats the phase-separated solvent B and contributes to the formation of primary particles.

The polymer C is not particularly restricted so long as it is soluble in the solvent A but insoluble in the solvent B.

Examples of the polymer C include ionic polymers, such as an anionic polymer, a cationic polymer, and a betaine polymer; and nonionic polymers.

[Anionic Polymer]

The anionic polymer has an anionic group. Examples of the anionic group include groups that are capable of releasing a hydrogen ion upon dissociation thereof to exhibit acidity, such as a carboxy group (—COOM), a sulfonic acid group (—SO$_3$M), and a phosphoric acid group (—OPO$_3$M$_2$), or dissociated ion forms of these groups (such as —COO$^-$, —SO$_3^-$, —OPO$_3^{2-}$, and —OPO$_3^-$M). In the aforementioned chemical formulae, M represents a hydrogen atom, an alkali metal, ammonium, or an organic ammonium.

The anionic polymer is preferably an anionic polymer CI containing a constitutional unit derived from a monomer having an acidic group (hereinafter also referred to as "anionic polymer CI").

The monomer having an acidic group is preferably a monomer having a carboxy group, more preferably at least one selected from the group consisting of (meth)acrylic acid, crotonic acid, itaconic acid, maleic acid, fumaric acid, citraconic acid, and 2-methacryloyloxymethyl succinic acid, and still more preferably (meth)acrylic acid.

Here, the term "(meth)acrylic acid" means at least one selected from the group consisting of acrylic acid and methacrylic acid.

The anionic polymer CI is preferably a copolymer further containing a constitutional unit derived from other monomer than the monomer having an acidic group. Examples of the other monomer include hydrophobic monomers, such as a (meth)acrylate having a hydrocarbon group derived from an aliphatic alcohol and an aromatic group-containing monomer; and nonionic monomers.

Here, the term "(meth)acrylate" means at least one selected from the group consisting of acrylates and methacrylates.

The (meth)acrylate having a hydrocarbon group derived from an aliphatic alcohol is one having a hydrocarbon group derived from an aliphatic alcohol having preferably 1 or more and 22 or less carbon atoms, more preferably 1 or more and 12 or less carbon atoms, and still more preferably 1 or more and 8 or less carbon atoms. Examples of the (meth)acrylate include a (meth)acrylate having a linear alkyl group; a (meth)acrylate having a branched alkyl group; and a (meth)acrylate having an alicyclic alkyl group.

The aromatic group-containing monomer is preferably a vinyl monomer having an aromatic group having 6 or more and 22 or less carbon atoms, which may have a substituent containing a hetero atom, and more preferably at least one selected from the group consisting of a styrene-based monomer and an aromatic group-containing (meth)acrylate. A molecular weight of the aromatic group-containing monomer is preferably less than 500.

Examples of the styrene-based monomer include styrene, α-methylstyrene, 2-methylstyrene, vinyltoluene, and divinylbenzene.

Examples of the aromatic group-containing (meth)acrylate include phenyl (meth) acrylate, benzyl (meth) acrylate, and phenoxyethyl (meth)acrylate.

Examples of the nonionic monomer in the anionic polymer CI include (meth)acrylamide; N-vinyl-2-pyrrolidone; diacetone acrylamide; an N-alkyl (meth)acrylamide; a hydroxyalkyl (meth)acrylate; a polyalkylene glycol (meth) acrylate (n=2 to 30, n represents an average addition molar number of the oxyalkylene group; hereinafter the same); an alkoxypolyalkylene glycol (meth)acrylate (n=1 to 30); a phenoxy(ethylene glycol/propylene glycol copolymer) (n=1 to 30, in which n for ethylene glycol: n=1 to 29) (meth) acrylate.

Specific examples of commercially available nonionic monomers include NK ESTER M-20G, NK ESTER M-40G, NK ESTER M-90G, NK ESTER M-230G and the like, all of which are manufactured by Shin-Nakamura Chemical Co., Ltd.; and BLEMMER PE-90, BLEMMER PE-200, BLEMMER PE-350 and the like, BLEMMER PME-100, BLEMMER PME-200, BLEMMER PME-400 and the like, BLEMMER PP-500, BLEMMER PP-800, BLEMMER PP-1000 and the like, BLEMMER AP-150, BLEMMER AP-400, BLEMMER AP-550 and the like, BLEMMER 50PEP-300, BLEMMER 50POEP-800B, BLEMMER 43PAPE-600B and the like, all of which are manufactured by NOF Corporation.

Each of the aforementioned monomers can be used alone or in combination of two or more thereof.

A weight average molecular weight of the anionic polymer CI is preferably 5,000 or more, more preferably 10,000 or more, and still more preferably 20,000 or more, and is also preferably 1,000,000 or less, more preferably 500,000 or less, and still more preferably 200,000 or less. The weight average molecular weight of the anionic polymer CI is a molecular weight measured by the gel permeation chromatography (GPC) as expressed in terms of polystyrene.

Examples of commercially available products of the anionic polymer CI include acrylic acid/acrylic acid alkyl ester/(N-alkyl) acrylamide copolymers, such as ULTRAHOLD 8, ULTRAHOLD STRONG, and ULTRAHOLD POWER (all of which are manufactured by BASF Japan Ltd.), and AMPHOMER V-42 (manufactured by National Starch & Chemical Co.); carboxyvinyl polymers, such as CARBOPOL 980 and CARBOPOL 981 (all of which are manufactured by Lubrizol Advanced Materials, Inc.); (meth) acrylic acid/(meth)acrylic acid alkyl ester copolymers, such as DIAHOLD (manufactured by Mitsubishi Chemical Corporation); (acrylic acid/diacetone acrylamide) copolymer AMP or (acrylic acid/acrylic acid alkyl ester/diacetone acrylamide) copolymer AMP, such as PLASCIZE L-53P, PLASCIZE L-75CB, PLASCIZE L-9540B, PLASCIZE L-6466, and PLASCIZE L-3200B (all of which are manufactured by Goo Chemical Co., Ltd.); and (meth)acrylic acid/acrylic acid alkyl ester/polyvinylpyrrolidone copolymers, such as LUVIFLEX VBM35 (manufactured by BASF SE).

The anionic polymer CI is preferably a copolymer containing a constitutional unit derived from a monomer having an acidic group and a constitutional unit derived from a (meth)acrylic acid alkyl ester; more preferably a copolymer containing a constitutional unit derived from a monomer having an acidic group, a constitutional unit derived from a (meth)acrylic acid alkyl ester, and a constitutional unit derived from an (N-alkyl) (meth)acrylamide; still more preferably a (meth)acrylic acid/(meth)acrylic acid alkyl ester/(N-alkyl) (meth)acrylamide copolymer; and yet still more preferably an acrylic acid/acrylic acid alkyl ester/(N-alkyl) acrylamide copolymer.

[Cationic Polymer]

In the present invention, the wording "cationic" of the cationic polymer means that in the case where a non-neutralized polymer is dispersed or dissolved in pure water, the pH becomes larger than 7; in the case of a polymer having a quaternary ammonium group or the like, when it is dispersed or dissolved in pure water while making its counter ion as a hydroxide ion, the pH becomes larger than 7; or in the case where a polymer or the like is insoluble in pure water, and the pH cannot be distinctly measured, a zeta potential of the dispersion having the polymer or the like dispersed in pure water becomes positive.

The cationic polymer preferably has a basic group, such as a primary, secondary, or tertiary amino group, a quaternary ammonium group, and a hydrazino group, and more preferably has a quaternary ammonium group.

The basic group includes ones neutralized with an acid, such as hydrochloric acid, sulfuric acid, nitric acid, acetic acid, formic acid, maleic acid, fumaric acid, citric acid, tartaric acid, adipic acid, and lactic acid.

Examples of the cationic polymer include a natural cationic polymer and a synthetic cationic polymer.

The natural cationic polymer is a polymer obtained through an operation, such as extraction and purification, from a natural product or one resulting through chemical modification of the foregoing polymer, and examples thereof include ones having a glucose residue in the polymer skeleton. Specifically, examples thereof include cationized guar gum, cationized tara gum, cationized locust bean gum, cationized cellulose, a cationized hydroxyalkyl cellulose, and a cationic starch.

Examples of the synthetic cationic polymer include polyethyleneimine, polyallylamine or an acid-neutralized product thereof, a polyglycol-polyamine condensate, cationic polyvinyl alcohol, cationic polyvinylpyrrolidone, a cationic silicone polymer, a 2-(dimethylamino)ethyl methacrylate polymer or an acid-neutralized product thereof, poly(trimethyl-2-methacryloyloxyethylammonium chloride), an amine/epichlorohydrin copolymer, an N,N-dimethylaminoethyl methacrylic acid diethyl sulfate/vinylpyrrolidone copolymer, an N,N-dimethylaminoethyl methacrylic acid diethyl sulfate/N,N-dimethyl acrylamide/dimethacrylic acid polyethylene glycol copolymer, polydiallydimethylammonium chloride, a diallyldimethylammonium chloride/acrylamide copolymer, a diallyldimethylammonium chloride/sulfur dioxide copolymer, a allyldimethylammonium chloride/hydroxyethyl cellulose copolymer, a 1-allyl-3-methylimidazolium chloride/vinylpyrrolidone copolymer, an alkylamino (meth)acrylate/vinylpyrrolidone copolymer, an alkylamino (meth)acrylate/vinylpyrrolidone/vinyl caprolactam copolymer, a (3-(meth)acrylamidopropyl)trimethylammonium chloride/vinylpyrrolidone copolymer, and an alkylamino alkyl acrylamide/alkyl acrylamide/(meth)acrylate/polyethylene glycol (meth)acrylate copolymer. These can be used alone or in combination of two or more thereof.

Above all, preferred are a cationic polymer CII-1 containing a constitutional unit derived from a monomer having a basic group (hereinafter also referred to as "cationic polymer CII-1") and a cationic silicone polymer CII-2.

[Cationic Polymer CII-1]

The cationic polymer CII-1 contains a constitutional unit derived from a monomer having a basic group. Examples of the foregoing basic group include the same groups as mentioned above.

Examples of the monomer having a basic group include amino group-containing monomers, such as an alkylamino (meth)acrylate, an N,N-dialkylaminoalkyl (meth)acrylate, N-[3-(dimethylamino)propyl] (meth)acrylamide, and a diallyldialkylammonium, and acid-neutralized products or quaternized products thereof. These can be used alone or in combination of two or more thereof.

Examples of the acid for acid neutralization include hydrochloric acid, sulfuric acid, nitric acid, acetic acid, formic acid, maleic acid, fumaric acid, citric acid, tartaric acid, adipic acid, and lactic acid; and examples of the quaternizing agent include alkyl halides, such as methyl chloride, ethyl chloride, methyl bromide, and methyl iodide, and alkylating agents, such as dimethyl sulfate, diethyl sulfate, and di-n-propyl sulfate.

The cationic polymer CII-1 is preferably a homopolymer of a monomer having a basic group, a copolymer of a monomer having a basic group and other monomer than the foregoing monomer having a basic group, or a polycondensate; more preferably a copolymer of a monomer having a basic group and other monomer than the foregoing monomer having a basic group; still more preferably a copolymer containing a constitutional unit derived from a monomer having a basic group, a constitutional unit derived from the hydrophobic group as exemplified above for the anionic polymer CI, and a constitutional unit derived from the nonionic monomer as exemplified above for the anionic polymer CI; and yet still more preferably a copolymer containing a constitutional unit derived from an amino group-containing monomer, a constitutional unit derived from a (meth)acrylic acid alkyl ester, a constitutional unit derived from an N-alkyl (meth)acrylamide, and a constitutional unit derived from an alkoxy polyethylene glycol mono(meth)acrylate. The cationic polymer CII-1 is produced by copolymerizing raw material monomers containing these monomers by a known polymerization method, such as a block polymerization method, a solution polymerization method, a suspension polymerization method, and an emulsion polymerization method. Of these polymerization methods, a solution polymerization method is preferred.

From the viewpoint of improving the whiteness and the concealment, at the time of producing the cationic polymer CII-1, the content of the monomer having a basic group, the hydrophobic monomer, and the nonionic monomer in the raw material monomers (the content as the non-neutralized content, hereafter the same), namely, the content of the constitutional unit derived from each of the components in the cationic polymer CII-1 is as follows.

The content of the monomer having a basic group is preferably 3% by mass, more preferably 5% by mass or more, and still more preferably 7% by mass or more, and is also preferably 35% by mass or less, more preferably 30% by mass or less, still more preferably 25% by mass or less, and yet still more preferably 20% by mass or less.

The content of the hydrophobic monomer is preferably 5% by mass or more, more preferably 10% by mass or more, and still more preferably 15% by mass or more, and is also preferably 35% by mass or less, more preferably 30% by mass or less, and still more preferably 25% by mass or less.

The content of the nonionic monomer is preferably 30% by mass or more, more preferably 40% by mass or more, and still more preferably 50% by mass or more, and is also preferably 85% by mass or less, more preferably 80% by mass or less, and still more preferably 75% by mass or less.

A weight average molecular weight of the cationic polymer CII-1 is preferably 5,000 or more, more preferably 7,000 or more, still more preferably 10,000 or more, yet still more preferably 50,000 or more, and even yet still more preferably 100,000 or more, and is also preferably 1,000,000 or less, more preferably 500,000 or less, still more preferably 300,000 or less, and yet still more preferably 200,000 or less, from the viewpoint of improving the whiteness and the concealment.

The weight average molecular weight of the cationic polymer CII-1 can be measured by the method described in the section of Examples.

[Cationic Silicone Polymer CII-2]

The cationic silicone polymer CII-2 is preferably a poly(N-acylalkyleneimine)/organopolysiloxane copolymer containing an organopolysiloxane segment (x) (hereinafter also referred to simply as "segment (x)") and a poly(N-acylalkyleneimine) segment (y) composed of an alkylene group containing a cationic nitrogen atom binding to at least one silicon atom of the segment (x) and a repeating unit of an N-acylalkyleneimine represented by following general formula (1-1) (the poly(N-acylalkyleneimine) segment (y) will be hereinafter also referred to simply as "segment (y)").

(1-1)

In the formula, $R^1$ represents a hydrogen atom, an alkyl group having 1 or more and 22 or less carbon atoms, an aryl group having 6 or more and 22 or less carbon atoms, or an arylalkyl group or alkylaryl group having 7 or more and 22 or less carbon atoms; and a is 2 or 3.

The alkyl group represented by $R^1$ is preferably an alkyl group having 1 or more and 12 or less carbon atoms, and more preferably an alkyl group having 1 or more and 3 or less carbon atoms, such as a methyl group, an ethyl group, a n-propyl group, and an isopropyl group.

Examples of the aryl group represented by $R^1$ include a phenyl group and a naphthyl group.

Examples of the arylalkyl group represented by $R^1$ include a phenylalkyl group and a naphthylalkyl group, in which the carbon number of the alkyl group is 1 or more and 20 or less; and examples of the alkylaryl group include an alkylphenyl group and an alkylnaphthyl group, in which the carbon number of the alkyl group is 1 or more and 20 or less.

Although a degree of polymerization of the repeating unit represented by the general formula (1-1) in the segment (y), for example, it is preferably 1 or more and 500 or less, and more preferably 6 or more and 100 or less.

Examples of the organopolysiloxane that forms the segment (x) include compounds represented by the following general (1-2).

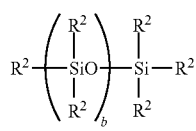

In the formula, $R^2$ represents an alkyl group having 1 or more and 22 or less carbon atoms, a phenyl group, or an alkyl group containing a nitrogen atom; though a plurality of the $R^2$ groups may be the same as or different from each other, at least one of them is an alkyl group containing a cationic nitrogen atom; and b is 100 or more and 5,000 or less.

In the general formula (1-2), among the alkyl groups having 1 or more and 22 or less carbon atoms as represented by $R^2$, an alkyl group having 1 or more and 12 or less carbon atoms is preferred, an alkyl group having 1 or more and 3 or less carbon atoms is more preferred, and a methyl group is still more preferred.

Examples of the alkyl group containing a nitrogen atom as represented by $R^2$ include alkyl groups having 2 or more and 20 or less carbon atoms which contains preferably 1 or more and 3 or less nitrogen atoms. The alkyl group containing a nitrogen atom may be existent in at least one silicon atom at an end or in a side chain of the organopolysiloxane, and the number of alkyl groups containing a nitrogen atom in the organopolysiloxane is preferably 1 or more and 300 or less, and more preferably 1 or more and 100 or less.

In the general formula (1-2), b is preferably 100 or more and 2,000 or less, and more preferably 350 or more and 1,500 or less.

A weight average molecular weight of the organopolysiloxane that forms the segment (x) is preferably 1,000 or more, more preferably 10,000 or more, and still more preferably 30,000 or more, and is also preferably 1,000,000 or less, more preferably 500,000 or less, and still more preferably 200,000 or less.

Examples of the alkylene group containing a nitrogen atom intervening in the bonding between the segment (x) and the segment (y) include alkylene groups having 2 or more and 20 or less carbon atoms which contains preferably 1 or more and 3 or less nitrogen atoms.

Specifically, examples of the nitrogen atom existing between carbon and carbon of the alkylene chain or at an end of the alkylene chain include (i) a secondary amine or a tertiary amine, (ii) an ammonium salt in which a hydrogen ion is added to a secondary amine or a tertiary amine, and (iii) a quaternary amine salt.

The poly(N-acylalkyleneimine)/organopolysiloxane copolymer is preferably one in which the segment (y) is bound to at least one silicon atom at an end or in a side chain of the segment (x) via the alkylene group containing a cationic nitrogen atom.

A mass ratio of the content of the segment (x) to the total content of the segment (x) and the segment (y) [{content of segment (x)}/{total content of segment (x) and segment (y)}] in the poly(N-acylalkyleneimine)/organopolysiloxane copolymer is preferably 0.1 or more, more preferably 0.3 or more, still more preferably 0.4 or more, and yet still more preferably 0.5 or more, and is also preferably 0.99 or less, more preferably 0.95 or less, and still more preferably 0.9 or less, from the viewpoint of improving the whiteness and the concealment.

In this specification, the mass ratio [{content of segment (x)}/{total content of segment (x) and segment (y)}] is a ratio of a mass (Mx) of the segment (x) to the total amount of a mass (Mx) of the segment (x) and a mass (My) of the segment (y) in the poly(N-acylalkyleneimine)/organopolysiloxane copolymer.

The mass ratio [{content of segment (x)}/{total content of segment (x) and segment (y)}] can be determined by dissolving 5% by mass of the poly(N-acylalkyleneimine)/organopolysiloxane copolymer in deuterated chloroform and calculating an integration ratio of an alkyl group or a phenyl group in the segment (x) and a methylene group in the segment (y) through a nuclear magnetic resonance ($^1$H-NMR) analysis.

A weight average molecular weight of the poly(N-acylalkyleneimine)/organopolysiloxane copolymer is preferably 10,000 or more, more preferably 50,000 or more, and still more preferably 70,000 or more, and is also preferably 1,000,000 or less, more preferably 500,000 or less, and still more preferably 200,000 or less, from the viewpoint of improving the whiteness and the concealment. The weight average molecular weight of the poly(N-acylalkyleneimine)/organopolysiloxane copolymer can be calculated from the weight average molecular weight of the organopolysiloxane that forms the segment (x) and the aforementioned mass ratio [{content of segment (x)}/{total content of segment (x) and segment (y)}].

Suitable examples of the poly(N-acylalkyleneimine)/organopolysiloxane copolymer include a poly(N-formylethyleneimine)/organopolysiloxane copolymer, a poly(N-acetylethyleneimine)/organopolysiloxane copolymer, and a poly(N-propionylethyleneimine)/organopolysiloxane copolymer.

The poly(N-acylalkyleneimine)/organopolysiloxane copolymer can be, for example, obtained by a method of allowing the (N-acylalkyleneimine) that is a ring-opening polymer of a cyclic imino ether and the organopolysiloxane that forms the segment (x) to react with each other. More specifically, the poly(N-acylalkyleneimine)/organopolysiloxane copolymer can be, for example, obtained by the method described in JP 2011-126978 A. The poly(N-acylalkyleneimine)/organopolysiloxane copolymer to be used as the cationic silicone polymer CII-2 can be used alone or in combination of two or more thereof.

[Betaine Polymer]

In the present invention, examples of the betaine polymer include a copolymer of a monomer having an anionic group and a monomer having a cationic group, a polymer or copolymer of a betaine monomer, a polymer having an anionic group introduced into a cationic polymer, and a polymer having the aforementioned basic group introduced into an anionic polymer. Above all, preferred is a polymer containing a betaine structure in a side chain thereof, and more preferred is a betaine polymer CIII containing a constitutional unit derived from a betaine monomer.

The betaine monomer is preferably a monomer containing a betaine structure and a (meth)acrylamide structure, more preferably at least one selected from the group consisting of a carboxybetaine monomer, a sulfobetaine monomer, and a phosphobetaine monomer, and still more preferably a carboxybetaine monomer.

Examples of the betaine polymer include polymethacryloylethyl dimethylbetaine, an N-methacryloyloxyethyl-N,N-dimethylammonium-α-N-methylcarboxybetaine/methacrylic acid alkyl ester copolymer, a methacryloylethyldimethylbetaine/methacryloylethyltrimethylammonium chloride/2-hydroxyethyl methacrylate copolymer, a methacryloylethyldimethylbetaine/methacryloyethyltrimethylammonium chloride/methacrylic acid/methoxypolyethylene glycol copolymer, and an octylacrylamide/acrylate/butylaminoethyl methacrylate copolymer. Above all, an N-methacryloyloxyethyl-N,N-dimethylammonium-α-N-methylcarboxybetaine/methacrylic acid alkyl ester copolymer is preferred.

A weight average molecular weight of the betaine polymer is preferably 5,000 or more, and more preferably 10,000 or more, and is also preferably 1,000,000 or less, more preferably 500,000 or less, and still more preferably 300,000 or less, from the viewpoint of improving the whiteness and the concealment. The weight average molecular weight of the betaine polymer is a molecular weight measured by the gel permeation chromatography (GPC) as expressed in terms of polystyrene.

Examples of commercially available betaine polymers include PLASCIZE L-410W, PLASCIZE L-402W, PLASCIZE L-440, PLASCIZE L-440W, PLASCIZE K-450, and PLASCIZE L-450W (all of which are a trade name, manufactured by Goo Chemical Co., Ltd.); YUKA FORMER SM and YUKA FORMER 301 (all of which are a trade name, manufactured by Mitsubishi Chemical Corporation); RAM RESIN-1000, RAM RESIN-2000, RAM RESIN-3000, and RAM RESIN-4000 (all of which are a trade name, manufactured by Osaka Organic Chemical Industry Ltd.); MERQUAT PLUS 3330 (a trade name, manufactured by Lubrizol Japan Ltd.); and UNFOAMER 28-4910 and UNFOAMER LV-71 (all of which are a trade name, manufactured by Akzo Nobel N.V.).

[Nonionic Polymer]

Examples of the nonionic polymer include polymers having a constitutional unit derived from a nonionic monomer; and water-soluble polysaccharides (such as a cellulose-based polymer, a gum-based polymer, and a starch-based polymer) and derivatives thereof.

Examples of the nonionic monomer in the nonionic polymer include (meth)acrylates having a hydrocarbon group derived from an aliphatic alcohol having 1 or more and 22 or less carbon atoms; N-vinyl-2-pyrrolidone; vinyl alcohol; polyalkylene glycol (meth)acrylates (n=1 to 30); alkoxypolyalkylene glycol mono(meth)acrylates (n=1 to 30); and (meth)acrylamides and derivatives thereof.

The nonionic polymer may further contain a constitutional unit derived from other monomer than the nonionic monomer. Examples of the other monomer include the aforementioned styrene-based monomers; the aforementioned aromatic group-containing (meth)acrylates; and vinyl acetate.

Specifically, examples of the nonionic polymer include polyvinyl alcohol, polyvinyl acetal, polyurethanepolyurea, polyvinylpyrrolidone, copolymers of vinylpyrrolidone and other nonionic monomer, such as a vinylpyrrolidone/vinyl acetate copolymer, cellulose-based polymers, such as a hydroxyalkyl cellulose, polyethylene glycol, polypropylene glycol, polyglycerin, polyvinyl alcohol, pullulan, guar gum, poly(N,N-dimethylacrylamide), poly(N-vinylacetamide), poly(N-vinylformamide), and a poly(2-alkyl-2-oxazoline). Above all, polyvinyl acetal and polyurethanepolyurea are preferred.

Examples of commercially available nonionic polymers include polyvinyl butyral, such as S-LEC B Series (which are a trade name, manufactured by Sekisui Chemical Co., Ltd.); polyurethanepolyurea, such as BAYCUSAN Series (which are a trade name, manufactured by Covestro Japan Ltd.); hydroxyethyl cellulose, such as HEC DAICEL SE900, HEC DAICEL SE850, HEC DAICEL SE600, HEC DAICEL 5E550, and HEC DAICEL SE400 (all of which are a trade name, manufactured by Daicel FineChem Ltd.); highly polymerized polyethylene glycol, such as POLYOX WSR N-12, POLYOX WSR N-60K, and POLYOX WSR 301 (all of which are a trade name, manufactured by The Dow Chemical Company); PEO-27, PEO-18, PEO-15, and PEO-8 (all of which are a trade name of polyethylene oxide, manufactured by Sumitomo Seika Chemicals Co., Ltd.); polyvinylpyrrolidone, such as LUVISKOL K90, LUVISKOL K80, and LUVISKOL K30 (all of which are a trade name, manufactured by BSAF SE); and polyvinyl alcohol, such as GOHSENOL Series (which are a trade name, manufactured by The Nippon Synthetic Chemical Industry Co., Ltd.).

In the present invention, from the viewpoint of improving the whiteness and the concealment, the dissolved amount of the polymer C in water is preferably less than 5 g in terms of the dissolved amount when the polymer C after drying at 105° C. for 2 hours and reaching a constant weight is dissolved in 100 g of water at 25° C. until it is saturated.

In the case where the polymer C is an anionic polymer, the aforementioned dissolved amount is the dissolved amount when the anionic group of the polymer C is neutralized with sodium hydroxide to an extent of 100%. In the case where the polymer C is a cationic polymer, the aforementioned dissolved amount is the dissolved amount when the cationic group of the polymer C is neutralized with hydrochloric acid to an extent of 100%.

In the present invention, from the viewpoint of improving the whiteness and the concealment, the polymer C is preferably an amphipathic polymer which is insoluble in the solvent B but has affinity to the solvent B and which also has affinity to water; and more preferably an ionic polymer. It is still more preferred that the polymer C contains a polymer containing, as the monomer constitutional unit, at least one selected from the group consisting of a monomer having an acidic group, a monomer having a basic group, and a betaine monomer; and it is yet still more preferred that the polymer C contains at least one selected from the group consisting of the anionic polymer CI, the cationic polymer CII-1, the cationic silicone polymer CII-2, and the betaine polymer CIII.

Above all, the polymer C is preferably a combination of two or more polymers; more preferably one containing the anionic polymer CI and at least one selected from the group consisting of the cationic polymer CII-1, the cationic silicone polymer CII-2, and the betaine polymer CIII; still more preferably one containing the anionic polymer CI and the cationic polymer CII-1 or the betaine polymer CIII; and yet still more preferably one containing the anionic polymer CI and the betaine polymer CIII.

A viscosity at 20° C. of the cosmetic composition is preferably 1 mPa·s or more, more preferably 5 mPa·s or more, and still more preferably 10 mPa·s or more, and is also preferably 1,000 mPa·s or less, more preferably 700 mPa·s or less, still more preferably 300 mPa·s or less, yet still more preferably 100 mPa·s or less, even yet still more preferably 50 mPa·s or less, and even still more preferably 30 mPa·s or less. The viscosity at 20° C. of the cosmetic composition is measured by the method described in the section of Examples.

The cosmetic composition of the present invention may also contain, as an arbitrary component, a component which is used for cosmetic compositions, such as a dye, an organic pigment, an inorganic pigment, an ultraviolet scattering agent, an ultraviolet absorber, a fragrance, a beauty ingredient, a medicinal ingredient, a pH control agent, a moisturizer, an antioxidant, a disinfectant, and an antiseptic agent. Each of them may be used alone or in combination of two or more.

(Production of Cosmetic Composition)

The cosmetic composition can be obtained by mixing the solvent A, the solvent B, and the polymer C, and optionally, the aforementioned arbitrary component, followed by stirring. Although the mixing order is not particularly restricted, it is preferable to include a step of first mixing the solvent A and the polymer C to dissolve the polymer C in the solvent A, thereby obtaining a solution of the polymer C, and then adding the solvent B to the foregoing solution. If desired, the aforementioned arbitrary component may be further added and mixed.

From the viewpoint of improving the whiteness and the concealment, the content of each of the components in the cosmetic composition is as follows.

The content of the solvent A in the cosmetic composition is preferably 50% by mass or more, more preferably 60% by mass or more, and still more preferably 70% by mass or more, and is also preferably 90% by mass or less, more preferably 85% by mass or less, and still more preferably 80% by mass or less.

The content of the solvent B in the cosmetic composition is preferably 5% by mass or more, more preferably 10% by mass or more, and still more preferably 15% by mass or more, and is also preferably 40% by mass or less, more preferably 30% by mass or less, and still more preferably 25% by mass or less.

A mass ratio of the content of the solvent A to the solvent B in the cosmetic composition [(solvent A)/(solvent B)] is preferably 0.01 or more, more preferably 0.1 or more, still more preferably 0.5 or more, yet still more preferably 1 or more, even yet still more preferably 1.5 or more, and even still more preferably 2 or more, and is also preferably 50 or less, more preferably 30 or less, still more preferably 10 or less, yet still more preferably 7 or less, and even yet still more preferably 5 or less.

The content of the polymer C in the cosmetic composition is preferably 2% or more, more preferably 3% by mass or more, and still more preferably 4% by mass or more, and is also preferably 15% by mass or less, more preferably 10% by mass or less, and still more preferably 8% by mass or less.

In the case where the polymer C contains the anionic polymer CI and at least one selected from the group consisting of the cationic polymer CII-1, the cationic silicone polymer CII-2, and the betaine polymer CIII, the total content of the anionic polymer CI and at least one selected from the group consisting of the cationic polymer CII-1, the cationic polymer CII-2, and the betaine polymer CIII in the polymer C, or the total content of the anionic polymer CI, the cationic polymer CII-1, the cationic silicone polymer CII-2, and the betaine polymer CIII in the polymer C is preferably 60% by mass or more, more preferably 70% by mass or more, still more preferably 80% by mass or more, and yet still more preferably 90% by mass or more, and is also preferably 100% by mass or less, and yet still more preferably 100% by mass.

In the case where the polymer C contains the anionic polymer CI and the betaine polymer CIII, a mass ratio of content between the anionic polymer CI and the betaine polymer CIII [(content of anionic polymer CI)/(content of betaine polymer CIII)] is preferably 0.1 or more, more preferably 0.3 or more, still more preferably 0.5 or more, and yet still more preferably 0.7 or more, and is also preferably 9 or less, more preferably 5 or less, still more preferably 3 or less, and yet still more preferably 2 or less.

A mass ratio of the content of the polymer C to the total content of the solvent A and the solvent B in the cosmetic composition [(polymer C)/{(solvent A)+(solvent B)}] is preferably 0.01 or more, more preferably 0.03 or more, and still more preferably 0.05 or more, and is also preferably 1 or less, more preferably 0.5 or less, still more preferably 0.3 or less, yet still more preferably 0.2 or less, and even yet still more preferably 0.1 or less.

The content of the inorganic pigment in the cosmetic composition of the present invention is preferably 10% by mass or less, more preferably 5% by mass or less, still more preferably 3% by mass or less, yet still more preferably 1% by mass or less, and even yet still more preferably 0% by mass.

The cosmetic composition of the present invention can be applied to the skin exclusive of head hair, and preferably any of face, hand and foot, body, and so on, and preferably, it can be used by means of coating. According to this, natural brightness can be given to the skin.

The cosmetic composition of the present invention can be suitably utilized for skin cosmetics, such as a makeup base cosmetic, a foundation, a concealer; an ultraviolet-light shielding cosmetic, e.g., a sunscreen milk lotion and a sunscreen cream; a makeup cosmetic, e.g., a cheek rouge, an eye shadow, a mascara, an eyeliner, an eyebrow, an overcoat agent, and a lipstick; a skin cleansing cosmetic, e.g., a facial cleanser and a cleansing cosmetic; and a basic cosmetic, e.g., a liquid cosmetic, a beauty pack, and a massage cosmetic. Above all, the cosmetic composition of the present invention is preferably applied for a makeup base cosmetic, a foundation, and so on.

As for a preparation form of the cosmetic composition of the present invention, it is possible to adapt for a cream form, a gel form, a milk lotion form, a solution form, a paste form, a solid form, a multilayered form, etc. Further, the cosmetic composition of the present invention can be applied as a sheet agent, a spray agent, or a mousse agent.

[Cosmetic Coating Film for Skin]

The cosmetic coating film for skin of the present invention is formed of the aforementioned cosmetic composition.

The aforementioned cosmetic coating film can be formed by coating the aforementioned cosmetic composition on the skin surface under temperature and humidity conditions for daily living by a method which is typically adopted on the occasion of applying a cosmetic composition to the skin, to form a coating film and then drying the foregoing coating film under atmospheric pressure conditions.

An applied amount of the cosmetic composition to the skin is preferably 1 mg/cm$^2$ or more, more preferably 2 mg/cm$^2$ or more, and still more preferably 3 mg/cm$^2$ or more, and is also preferably 10 mg/cm$^2$ or less, more preferably 7 mg/cm$^2$ or less, and still more preferably 5 mg/cm$^2$ or less.

A thickness of the coating film before drying (hereinafter also referred to as "wet film thickness") is preferably 10 μm or more, more preferably 20 μm or more, and still more preferably 30 μm or more, and is also preferably 300 μm or less, more preferably 200 μm or less, still more preferably 100 μm or less, and yet still more preferably 50 μm or less.

In the present invention, though drying of the coating film can be thoroughly performed by means of natural drying at a skin temperature, it may be performed by means of blast drying, warm air drying, or the like from the viewpoint of quickly the drying.

In the case of performing warm air drying, though the temperature of the warm air is not particularly restricted, it is preferably 40° C. or higher, more preferably 50° C. or higher, and still more preferably 55° C. or higher, and is also preferably 80° C. or lower, more preferably 70° C. or lower, and still more preferably 65° C. or lower.

A drying time of the coating film is preferably 5 minutes or more, more preferably 7 minutes or more, and still more preferably 10 minutes or more, and is also preferably 30 minutes or less, and more preferably 20 minutes or less.

On the occasion of drying the coating film, from the viewpoint of improving the whiteness and the concealment, it is preferred to atomize fine droplets of the liquid containing water on the skin surface by using an apparatus of generating the droplets. According to this, the phase separation between the solvent A and the solvent B quickly proceeds, and the formation of the primary particles in which the solvent B is coated with the polymer C is accelerated. The apparatus of generating fine droplets is not particularly limited, and for example, it is preferred to use an atomizer, such as a jet type atomizer, an ultrasonic atomizer, and a mesh type atomizer.

The liquid to be atomized contains water, but it may also contain other liquid than water.

As for the other liquid, a monohydric alcohol having 1 or more and 4 or less carbon atoms is preferred, and example thereof include ethanol, propanol, isopropanol, and tert-butyl alcohol. Above all, preferred is at least one selected from the group consisting of ethanol, propanol, isopropanol, and tert-butyl alcohol, more preferred is ethanol from the viewpoint of improving the whiteness and the concealment.

The content of water in the liquid to be atomized is preferably 50% by mass or more, more preferably 70% by mass or more, and still more preferably 90% by mass or more, and is also preferably 100% by mass or less, and yet still more preferably 100% by mass.

An applied amount of the fine droplets to be atomized is preferably 0.01 mg/cm$^2$ or more, more preferably 0.05 mg/cm$^2$ or more, and still more preferably 0.1 mg/cm$^2$ or more, and is also preferably 10 mg/cm$^2$ or less, more preferably 7 mg/cm$^2$ or less, and still more preferably 5 mg/cm$^2$ or less.

An average diameter of the fine droplets to be atomized is preferably 0.01 μm or more, more preferably 0.1 μm or more, and still more preferably 1 lam or more, and is also preferably 50 μm or less, more preferably 30 μm or less, and still more preferably 10 μm or less.

EXAMPLES

In the following Synthesis Examples, Preparation Examples, Examples, and Comparative Examples, the terms "parts" and "%" are "parts by mass" and "% by mass", respectively unless otherwise indicated. The measurements of physical properties of polymers and so on were performed by the following methods.
(1) Measurement of Weight Average Molecular Weight of Cationic Polymer CII-1

The measurement was performed using, as an eluent, a liquid in which phosphoric acid and lithium bromide were dissolved in concentrations of 60 mmol/L and 50 mmol/L, respectively in N,N-dimethylformamide by means of the gel permeation chromatography [GPC apparatus (HLC-8320GPC), manufactured by Tosoh Corporation, columns (TSKgel Super AWM-H, TSKgel Super AW3000, TSKgel guardcolumn Super AW-H), manufactured by Tosoh Corporation, flow rate: 1 mL/min] while using, as a standard substance, mono-dispersed polystyrene kits having already-known molecular weights [PStQuick B (F-550, F-80, F-10, F-1, A-1000) and PStQuick C (F-288, F-40, F-4, A-5000, A-500), all of which are manufactured by Tosoh Corporation].

As a measurement sample, one prepared by mixing 0.1 g of the cationic polymer CII-1 and 10 mL of the aforementioned eluent in a glass vial, stirring the mixture with a magnetic stirrer at 25° C. for 10 hours, and filtering the resultant with a syringe filter (DISMIC-13HP PTFE, 0.2 μm, manufactured by Advantech Co., Ltd.) was used.
(2) Measurement of Number Average Molecular Weight of Poly(N-propionylethyleneimine)

The measurement was performed using, as an eluent, 1 mmol/L of FARMIN DM20 (a trade name, manufactured by Kao Corporation)/chloroform by means of the gel permeation chromatography [measurement columns: two columns (K-804L), manufactured by Showa Denko K.K., connected in series, flow rate: 1 mL/min, column temperature: 40° C., detector: differential refractometer] while using, as a standard substance, polystyrene having an already-known molecular weight. 100 μL of the measurement sample having a concentration of 5 mg/mL was used.
(3) Measurement of Viscosity The viscosity was measured with an E-type viscometer RE80, manufactured by Toki Sangyo Co., Ltd. at a rotation number of 100 rpm for a measurement time of 1 minute by using a standard rotor (1° 34'×R24).

The measurement of the viscosity was performed at 20° C. for hydrogenated polyisobutene, 25° C. for the silicone oil, and 20° C. for the cosmetic composition, respectively.
(4) Measurement of Wet Film Thickness T by Wire Bar-Coating In an environmental chamber, the temperature and humidity of which were controlled at a temperature of 25° C. and a humidity of 50%, an A4-sized transparent PET film (a trade name: LUMIRROR T-60, manufactured by Toray Industries, Inc., film thickness: 75 μm), the weight of which had been measured in advance, was placed on a desktop coater (a trade name: TC-1, manufactured by Mitsui Electric Co., Ltd.), and then, a wire bar to be wanted to confirm the wet film thickness was set. Subsequently, about 2 to 6 mL of a mixed solution of 10% of ethanol, 50% of water, and 40% of glycerin was dropped using a dropper, and immediately thereafter, the mixed solution was coated on the PET film using the above-set wire bar at a traveling speed of the wire bar of 1 m/min. On the occasion of coating, it was confirmed that the aforementioned mixed solution uniformly spread on the entire surface of the PET film, and the liquid leaked from the end. Subsequently, the weight of the coated PET film was immediately measured and corrected with a specific gravity of the aforementioned mixed solution, thereby calculating the wet film thickness T on the occasion of using the wire bar.

Details of the respective components are as follows.
(Anionic Polymer CI)

ULTRAHOLD 8: An acrylic acid/acrylic acid alkyl ester/ (N-alkyl) acrylamide copolymer (manufactured by BASF Japan Ltd., a trade name: ULTRAHOLD 8), powder with a solid component content of 100%

ULTRAHOLD STRONG: An acrylic acid/acrylic acid alkyl ester/(N-alkyl) acrylamide copolymer (manufactured by BASF Japan Ltd., a trade name: ULTRAHOLD STRONG), powder with a solid component content of 100%

ULTRAHOLD POWER-dry: A powder prepared by drying a solution of an acrylic acid/acrylic acid alkyl ester/(N-alkyl) acrylamide copolymer (solid component content: 32%) (manufactured by BASF Japan Ltd., a trade name: ULTRAHOLD POWER)

(Cationic Polymer CII-1)

Cationic polymer 1: A copolymer obtained in the following Synthesis Example 1

Cationic polymer 2: A copolymer obtained in the following Synthesis Example 2

(Cationic Silicone Polymer CII-2)

Cationic silicone polymer 1: A poly(N-propionylethyleneimine)/dimethylpolysiloxane copolymer obtained in the following Synthesis Example 3

Cationic silicone polymer 2: A poly(N-propionylethyleneimine)/dimethylpolysiloxane copolymer obtained in the following Synthesis Example 4

Cationic silicone polymer 3: A poly(N-propionylethyleneimine)/dimethylpolysiloxane copolymer obtained in the following Synthesis Example 5

(Betaine Polymer CIII)

YUKA FORMER SM-dry: A powder prepared by drying an ethanol solution of an N-methacryloyloxyethyl-N,N-dimethylammonium-α-N-methylcarboxybetaine/methacrylic acid alkyl ester copolymer (solid component content: 30%) (manufactured by Mitsubishi Chemical Corporation, a trade name: YUKA FORMER SM)

(Nonionic Polymer)

Polyvinyl butyral: S-LEC BM-1 (manufactured by Sekisui Chemical Co., Ltd., a trade name), powder with a solid component content of 100%

Polyurethanepolyurea: A powder prepared by drying BAYCUSAN C2000 (manufactured by Covestro Japan Ltd., a trade name, an ethanol solution of polyurethane-64 with a solid component content of 40%)

(Solvent B)

[Hydrocarbon Oil]

PARLEAM 3: Hydrogenated polyisobutene (manufactured by NOF Corporation, a trade name: PARLEAM 3, boiling point: 179° C., Ra: 45, viscosity: 1.4 mPa·s)

PARLEAM 4: Hydrogenated polyisobutene (manufactured by NOF Corporation, a trade name: PARLEAM 4, boiling point: 262° C., Ra: 45, viscosity: 3.7 mPa·s)

[Silicone Oil]

KF-96A-1cs: Trisiloxane (manufactured by Shin-Etsu Chemical Co., Ltd., a trade name: KF-96A-1cs, boiling point: 153° C., Ra: 45, viscosity: 0.9 m·Pas)

TMF-1.5: Methyltrimethicone (manufactured by Shin-Etsu Chemical Co., Ltd., a trade name: TMF-1.5, boiling point: 191° C., Ra: 45, viscosity: 1.4 m·Pas)

Synthesis Example 1 (Synthesis of Cationic Polymer 1)

In a reaction vessel equipped with two dropping funnels 1 and 2, monomers having a composition shown in the "Initially charged monomer solution" column of Table 1 were charged, followed by purging with a nitrogen gas.

Meanwhile, monomers and an organic solvent having a composition shown in the "Dropping monomer solution" column of Table 1 were mixed to prepare a dropping monomer solution; separately, an organic solvent and a polymerization initiator (2,2'-azobis(2,4-dimethylvaleronitrile): manufactured by Fujifilm Wako Pure Chemical Corporation, a trade name: V-65) were mixed to prepare a polymerization initiator solution; and they were charged in the dropping funnels 1 and 2, respectively, followed by purging with a nitrogen gas.

The initially charged monomer solution in the reaction vessel was kept at 62° C. in a nitrogen atmosphere while stirring, and the dropping monomer solution and the polymerization initiator solution were gradually dropped in the reaction vessel over 2 hours such that a proportion of the polymerization initiator to be dropped became constant relative to the monomers to be dropped.

After completion of dropping, the resultant was stirred for 1 hour while keeping at 62° C., and subsequently, 47 parts of acetone was added. The contents were further kept at 62° C. while stirring and thermally aged for 4 hours.

Subsequently, the unreacted monomers and the polymerization initiator residue were removed from the reaction product by using an ultrafiltration membrane (manufactured by NGK Insulators, Ltd., a ceramic-made ultrafiltration membrane, a trade name: CEFILT, pore diameter: 10 nm), and the residue was then dried to obtain a cationic amphipathic polymer (hereinafter also referred to as "cationic polymer 1"). A weight average molecular weight of the obtained cationic polymer 1 was 130,000.

Synthesis Example 2 (Synthesis of Cationic Polymer 2)

In a reaction vessel equipped with two dropping funnels 1 and 2, monomers having a composition shown in the "Initially charged monomer solution" column of Table 1 were charged, followed by purging with a nitrogen gas.

Meanwhile, monomers and an organic solvent having a composition shown in the "Dropping monomer solution" column of Table 1 were mixed to prepare a dropping monomer solution; and separately, a polymerization initiator (V-65) shown in the "Polymerization initiator solution" column of Table 1 were charged in the dropping funnels 1 and 2, respectively, followed by purging with a nitrogen gas.

The initially charged monomer solution in the reaction vessel was kept at 55° C. in a nitrogen atmosphere while stirring, and the dropping monomer solution and the polymerization initiator solution were gradually dropped in the reaction vessel over 2 hours such that a proportion of the polymerization initiator to be dropped became constant relative to the monomers to be dropped.

After completion of dropping, the contents were further kept at 55° C. while stirring and thermally aged for 5 hours.

Subsequently, the unreacted monomers and the polymerization initiator residue were removed from the reaction product by using an ultrafiltration membrane (manufactured by NGK Insulators, Ltd., a ceramic-made ultrafiltration membrane, a trade name: CEFILT, pore diameter: 10 nm), and the residue was then dried to obtain a cationic amphipathic polymer (hereinafter also referred to as "cationic polymer 2"). A weight average molecular weight of the obtained cationic polymer 2 was 120,000.

TABLE 1

|  |  | Synthesis Example 1 | | | Synthesis Example 2 | | |
| --- | --- | --- | --- | --- | --- | --- | --- |
|  |  | Reaction vessel Initially charged monomer solution | Dropping funnel 1 Dropping monomer solution | Dropping funnel 2 Polymerization initiator solution | Reaction vessel Initially charged monomer solution | Dropping funnel 1 Dropping monomer solution | Dropping funnel 2 Polymerization initiator solution |
| Monomer composition | DMAPAA *1 | 1.5 | 13.5 |  | 1.0 | 9.0 |  |
| (active ingredient) | Ethyl acrylate | 2.5 | 22.5 |  | 2.0 | 18.0 |  |
| (parts) | t-BuAAm *2 | 5.0 | 45.0 |  | 4.5 | 40.5 |  |
|  | NK ESTER M-90G *3 | 1.0 | 9.0 |  | 2.5 | 22.5 |  |
| Organic solvent | Acetone | 18.6 | 111.4 | 55.7 |  |  |  |
| (parts) | Ethanol |  |  |  | 10.0 | 60.0 | 30.0 |
| Polymerization initiator (parts) | V-65 *4 |  |  | 0.66 |  |  | 0.33 |
| Kind of cationic polymer CII-1 |  | Cationic polymer 1 | | | Cationic polymer 2 | | |
| Weight average molecular weight of cationic polymer CII-1 |  | 130,000 | | | 120,000 | | |

*1: N-[3-(Dimethylamino)propyl]acrylamide, manufactured by Sigma-Aldrich Co.
*2: N-tert-Butyl acrylamide, manufactured by Sigma-Aldrich Co.
*3: Methoxypolyethylene glycol monomethacrylate, manufactured by Shin-Nakamura Chemical Co., Ltd., a trade name: NK ESTER M-90G (ethylene oxide average addition molar number = 9, end: methyl group)
*4 2,2'-Azobis(2,4-dimethylvalelonitrile), manufactured by Fujifilm Wako Pure Chemical Corporation, a trade name: V-65

Synthesis Example 3 (Synthesis of Cationic Silicone Polymer 1)

12.9 g (0.13 mol) of 2-ethyl-2-oxazoline and 27.7 g of ethyl acetate were mixed, and the mixed liquid was dehydrated with 2.0 g of a molecular sieve (ZEOLUM A-4, manufactured by Tosoh Corporation) at 28° C. for 15 hours. To the resulting dehydrated ethyl acetate solution of 2-ethyl-2-oxazoline, 0.77 g (0.005 mol) of diethyl sulfate was added, and the contents were heat-refluxed in a nitrogen atmosphere at 80° C. for 8 hours, to obtain a terminal reactive poly(N-propionylethyleneimine) (number average molecular weight: 2,700) solution.

Separately, 100.0 g of side-chain primary aminopropyl-modified polydimethylsiloxane (manufactured by Shin-Etsu Chemical Co., Ltd., a trade name: KF-8015, weight average molecular weight: 100,000 (catalogue value), amine equivalent: 20,000) and 203.0 g of ethyl acetate were mixed, and the mixed liquid was dehydrated with 15.2 g of a molecular sieve at 28° C. for 15 hours.

Subsequently, the above-obtained terminal reactive poly(N-propionylethyleneimine) solution was collectively added to the side-chain primary aminopropyl-modified polydimethylsiloxane solution, and the contents were heat-refluxed at 80° C. for 10 hours. The obtained reaction mixture was concentrated under reduced pressure to obtain a poly(N-propionylethyleneimine)/dimethylpolysiloxane copolymer (hereinafter also referred to as "cationic silicone polymer 1") as a white rubber-like solid (108 g). A weight average molecular weight of the cationic silicone polymer 1 was 115,000 (calculated value), and a mass ratio [{content of organopolysiloxane segment (x)}/[total content of {organopolysiloxane segment (x)} and {poly(N-acylalkyleneimine) segment (y)}]] was 0.87.

Synthesis Example 4 (Synthesis of Cationic Silicone Polymer 2)

53.3 g (0.54 mol) of 2-ethyl-2-oxazoline and 127.5 g of ethyl acetate were mixed, and the mixed liquid was dehydrated with 9.0 g of a molecular sieve (ZEOLUM A-4, manufactured by Tosoh Corporation) for 15 hours. To the resulting dehydrated ethyl acetate solution of 2-ethyl-2-oxazoline, 9.48 g (0.061 mol) of diethyl sulfate was added, and the contents were heat-refluxed in a nitrogen atmosphere at 80° C. for 8 hours, to obtain a terminal reactive poly(N-propionylethyleneimine) (number average molecular weight: 1,300) solution.

Separately, 153.7 g of side-chain primary aminopropyl-modified polydimethylsiloxane (manufactured by Shin-Etsu Chemical Co., Ltd., a trade name: KF-8003, weight average molecular weight: 40,000 (catalogue value), amine equivalent: 2,000) and 312.1 g of ethyl acetate were mixed, and the mixed liquid was dehydrated with 23.3 g of a molecular sieve at 28° C. for 15 hours.

Subsequently, the above-obtained terminal reactive poly(N-propionylethyleneimine) solution was collectively added to the side-chain primary aminopropyl-modified polydimethylsiloxane solution, and the contents were heat-refluxed at 80° C. for 10 hours. The reaction mixture was concentrated under reduced pressure to obtain a poly(N-propionylethyleneimine)/dimethylpolysiloxane copolymer (hereinafter also referred to as "cationic silicone polymer 2") as a pale yellow rubber-like solid (200 g). A weight average molecular weight of the cationic silicone polymer 2 was 56,000 (calculated value), and a mass ratio [{content of organopolysiloxane segment (x)}/[total content of {organopolysiloxane segment (x)} and {poly(N-acylalkyleneimine) segment (y)}]] was 0.71.

Synthesis Example 5 (Synthesis of Cationic Silicone Polymer 3)

73.7 g (0.74 mol) of 2-ethyl-2-oxazoline and 156.0 g of ethyl acetate were mixed, and the mixed liquid was dehydrated with 12.0 g of a molecular sieve (ZEOLUM A-4, manufactured by Tosoh Corporation) at 28° C. for 15 hours. To the resulting dehydrated ethyl acetate solution of 2-ethyl-2-oxazoline, 2.16 g (0.014 mol) of diethyl sulfate was added, and the contents were heat-refluxed in a nitrogen atmosphere at 80° C. for 8 hours, to obtain a terminal reactive poly(N-propionylethyleneimine) (number average molecular weight: 6,000) solution.

Separately, 70.0 g of side-chain primary aminopropyl-modified polydimethylsiloxane (KF-864, manufactured by Shin-Etsu Silicone Co., Ltd., weight average molecular weight: 50,000 (catalogue value), amine equivalent: 3,800)

and 140.0 g of ethyl acetate were mixed, and the mixed liquid was dehydrated with 15.0 g of a molecular sieve at 28° C. for 15 hours.

Subsequently, the above-obtained terminal reactive poly(N-propionylethyleneimine) solution was collectively added to the side-chain primary aminopropyl-modified polydimethylsiloxane solution, and the contents were heat-refluxed at 80° C. for 10 hours. The reaction mixture was concentrated under reduced pressure to obtain a poly(N-propionylethyleneimine)/dimethylpolysiloxane copolymer (hereinafter also referred to as "cationic silicone polymer 3") as a white rubber-like solid (135 g). A weight average molecular weight of the cationic silicone polymer 3 was 100,000 (calculated value), and a mass ratio [{content of organopolysiloxane segment (x)}/[total content of {organopolysiloxane segment (x)} and {poly(N-acylalkyleneimine) segment (y)}]] was 0.50.

Examples 1-1 to 1-5 and Comparative Examples 1-1 to 1-7

<Production of Cosmetic Composition>

3 parts of ULTRAHOLD 8 and 3 parts of YUKA FORMER SM-dry as the polymer C were dissolved in the solvent A described in Table 2; after confirming that the solution was transparent and free from a floating material and a precipitate, the solvent B described in Table 2 was added; the contents were stirred and homogenized; and the resultant was filtered with a cellulose acetate syringe filter having pore diameter of 0.20 μm, manufactured by Advantech Co., Ltd. or a PTFE syringe filter, manufactured by the same company. There were thus obtained cosmetic compositions X-1 to X-5 and XC-1 to XC-7. As for the used filter, from the viewpoint of solvent resistance of the filter itself, the cellulose acetate syringe filter, manufactured by Advantech Co., Ltd. was used for the liquid compositions X-1 to X-5 and XC-1 to XC-2 and XC-7, and the PTFE syringe filter, manufactured by Advantech Co., Ltd. was used for the liquid compositions XC-3 to XC-6.

The dissolved amount of the polymer C used in Example 1-1 in 100 g of the solvent A was 50 g, and the dissolved amount thereof in 100 g of the solvent B was 0.3 g. In addition, the dissolved amount of the polymer C used in Examples 1-2 to 1-5 in 100 g of the solvent B was less than 5 g, and the dissolved amount thereof in 100 g of the solvent A was 5 g or more.

(Preparation of Cosmetic Coating Film)

In an environmental chamber, the temperature and humidity of which were controlled at a temperature of 25° C. and a humidity of 50%, a glass substrate (manufactured by Matsunami Glass Ind., Ltd., MAS-coated slide glass 59215) was fixed on a desktop coater (manufactured by Mitsui Electric Co., Ltd., TC-1) such that the MAS-coated surface was positioned at the front surface side; 1 mL of each of the cosmetic compositions was dropped on the end of the slide glass; and immediately thereafter, the respective cosmetic compositions were coated on the glass substrate using a No. 16 wire bar at a traveling speed of 1 m/min such that the thickness of the coating film before drying was 36.6 μm. On the occasion of coating, fine droplets of ion-exchanged water were blown onto the coating surface by using an ultrasonic nebulizer (manufactured by Shin-Ei Industries, Inc., a trade name: COMFORT OASIS, model No.: KU-200, average particle diameter of droplets: 1 to 5 μm) so as to follow the wire bar simultaneously with the coating; the wire bar was transported to the end of the glass substrate; and at the point of time when the wire bar fell from the glass substrate, a power source of the ultrasonic nebulizer was turned off, thereby terminating the atomization of droplets.

The glass substrate after coating the cosmetic composition and atomizing the droplets of ion-exchanged water was allowed to stand for 30 minutes in an environmental chamber, the temperature and humidity of which were controlled at a temperature of 25° C. and a humidity of 50%. There were thus obtained in cosmetic coating films 1-1 to 1-5 and 1-C1 to 1-C7 formed of the respective cosmetic compositions.

[Evaluation of Whiteness]

In conformity with JIS K5101-42004, one sheet of each of the obtained cosmetic coating films formed on the glass substrate was placed in a black part of a hiding-chart, and a black image density was measured. As a measuring device of the image density, a spectrophotometer/densitometer (manufactured by X-Rite, Inc., a trade name: SpectroEye) was used. The measurement condition was light source: D65, observation field: 2°, density standard: DIN, white base: "Abs", and built-in filter: "No". The results are shown in Table 2.

As a result of measurement of the non-coated glass substrate, a measured value was 2.25. It is indicated that the smaller the measured value, the higher the whiteness, and the more excellent the concealment. The measured value is preferably 1 or less, and in this case, the whiteness is high, and the concealment is excellent.

TABLE 2

| | | | | | | Example | | | | Comparative Example | | | | Example | Comparative Example | | |
|---|---|---|---|---|---|---|---|---|---|---|---|---|---|---|---|---|---|
| | | | | | | 1-1 | 1-2 | 1-3 | 1-4 | 1-1 | 1-2 | 1-3 | 1-4 | 1-5 | 1-5 | 1-6 | 1-7 |
| | | | | | | X-1 | X-2 | X-3 | X-4 | XC-1 | XC-2 | XC-3 | XC-4 | X-5 | XC-5 | XC-6 | XC-7 |
| Cosmetic composition No. | | | | | | | | | | | | | | | | | |
| Composition (parts) | Solvent A | Kind | | Boiling point (° C.) | Ra | | | | | | | | | | | | |
| | | Ethanol | | 78 | 24 | 84 | | | | | | | | 84 | 84 | 84 | 94 |
| | | Propanol | | 97 | 27 | | 84 | | | | | | | | | | |
| | | Isopropanol | | 82 | 28 | | | 84 | | | | | | | | | |
| | | tert-Butyl alcohol | | 82 | 30 | | | | 84 | | | | | | | | |
| | | Butanol | | 118 | 28 | | | | | 84 | | | | | | | |
| | | Pentanol | | 138 | 30 | | | | | | 84 | | | | | | |
| | | Chloroform | | 61 | 39 | | | | | | | 84 | | | | | |
| | | Toluene | | 111 | 43 | | | | | | | | 84 | | | | |
| | Solvent B | Kind | | Boiling point (° C.) | Ra | | | | | | | | | | | | |

TABLE 2-continued

|  |  |  |  | Example |  |  |  | Comparative Example |  |  |  | Example | Comparative Example |  |  |
|---|---|---|---|---|---|---|---|---|---|---|---|---|---|---|---|
|  |  |  |  | 1-1 X-1 | 1-2 X-2 | 1-3 X-3 | 1-4 X-4 | 1-1 XC-1 | 1-2 XC-2 | 1-3 XC-3 | 1-4 XC-4 | 1-5 X-5 | 1-5 XC-5 | 1-6 XC-6 | 1-7 XC-7 |
|  |  | PARLEAM 3 | 179 45 | 10 | 10 | 10 | 10 | 10 | 10 | 10 | 10 |  |  |  |  |
|  |  | Isododecane | 177 45 |  |  |  |  |  |  |  |  | 10 |  |  |  |
|  |  | Hexane | 69 45 |  |  |  |  |  |  |  |  |  | 10 |  |  |
|  |  | Dimethyl-formamide | 153 31 |  |  |  |  |  |  |  |  |  |  | 10 |  |
|  | Polymer C | ULTRAHOLD 8 |  | 3 | 3 | 3 | 3 | 3 | 3 | 3 | 3 | 3 | 3 | 3 | 3 |
|  |  | YUKA FORMER SM-dry |  | 3 | 3 | 3 | 3 | 3 | 3 | 3 | 3 | 3 | 3 | 3 | 3 |
| Viscosity of cosmetic composition (mPa·s) |  |  |  | 12.2 | 24.3 | 18.7 | 15.5 | 39.3 | 87.3 | 42.2 | 6.8 | 11.8 | 10.3 | 10.2 | 10.0 |
| Evaluation | Cosmetic coating film No. |  |  | 1-1 | 1-2 | 1-3 | 1-4 | 1-C1 | 1-C2 | 1-C3 | 1-C4 | 1-5 | 1-C5 | 1-C6 | 1-C7 |
|  | Whiteness (image density) |  |  | 0.41 | 0.91 | 0.69 | 0.54 | 2.22 | 2.31 | 1.71 | 1.81 | 0.69 | 1.99 | 2.16 | 2.21 |

From Table 2, in Examples 1-1 to 1-5, a high whiteness was revealed, and high concealment was exhibited even without containing an inorganic pigment. On the other hand, in Comparative Examples 1-1 to 1-7, in view of the fact that the whiteness was low, the desired concealment was not expressed.

Examples 2-1 to 2-30

(Production of Cosmetic Composition)

Each of the polymers C shown in Table 3 and Table 4 was dissolved in absolute ethanol as the solvent A; after confirming that the solution was transparent and free from a floating material and a precipitate, PARLEAM 3 was added as the solvent B; the contents were stirred and homogenized; and the resultant was filtered with a cellulose acetate syringe filter having a pore diameter of 0.20 μm, manufactured by Advantech Co., Ltd. There were thus obtained cosmetic compositions Y-1 to Y-30.

The dissolved amount of each of the polymers C used in Examples 2-1 to 2-30 in 100 g of the solvent B was less than 5 g, and the dissolved amount thereof in 100 g of the solvent A was 5 g or more.

(Preparation of Cosmetic Coating Film and Evaluation of Whiteness)

Cosmetic coating films 2-1 to 2-30 were prepared and evaluated for the whiteness in the same manners as mentioned above. The results are shown in Table 3 and Table 4.

TABLE 3

|  |  |  |  | Example |  |  |  |  |  |  |  |  |  |  |
|---|---|---|---|---|---|---|---|---|---|---|---|---|---|---|
|  |  |  |  | 2-1 Y-1 | 2-2 Y-2 | 2-3 Y-3 | 2-4 Y-4 | 2-5 Y-5 | 2-6 Y-6 | 2-7 Y-7 | 2-8 Y-8 | 2-9 Y-9 | 2-10 Y-10 | 2-11 Y-11 |
| Cosmetic composition No. |  |  |  |  |  |  |  |  |  |  |  |  |  |  |
| Composition (parts) | Solvent A | Ethanol |  | 74 | 74 | 74 | 74 | 74 | 74 | 74 | 74 | 74 | 74 | 74 |
|  | Solvent B | PARLEAM 3 |  | 20 | 20 | 20 | 20 | 20 | 20 | 20 | 20 | 20 | 20 | 20 |
|  | Polymer C | Anionic polymer CI | ULTRAHOLD 8 |  | 6 |  |  |  |  |  | 3 |  |  |  |
|  |  |  | ULTRAHOLD STRONG |  |  | 6 |  |  |  |  |  | 3 |  |  |
|  |  |  | ULTRAHOLD POWER dry |  |  |  | 6 |  |  |  |  |  | 3 |  |
|  |  | Cationic polymer CII-1 | Cationic polymer 1 |  |  |  |  | 6 |  |  |  |  |  | 3 |
|  |  |  | Cationic polymer 2 |  |  |  |  |  |  | 6 |  |  |  | 3 |
|  |  | Betaine polymer CIII | YUKA FORMER SM-dry | 6 |  |  |  |  |  |  | 3 | 3 | 3 | 3 |
| Viscosity of cosmetic composition (mPa·s) |  |  |  | 7.0 | 2.9 | 5.1 | 9.3 | 16.3 | 19.7 | 13.1 | 94.3 | 11.4 | 7.3 | 8.1 |
| Evaluation | Cosmetic coating film No. |  |  | 2-1 | 2-2 | 2-3 | 2-4 | 2-5 | 2-6 | 2-7 | 2-8 | 2-9 | 2-10 | 2-11 |
|  | Whiteness (image density) |  |  | 0.53 | 0.83 | 0.88 | 0.83 | 0.82 | 0.85 | 0.26 | 0.45 | 0.70 | 0.52 | 0.48 |

TABLE 4

|  |  |  | Example |  |  |  |  |  |  |  |  |  |
|---|---|---|---|---|---|---|---|---|---|---|---|---|
|  |  |  | 2-12 Y-12 | 2-13 Y-13 | 2-14 Y-14 | 2-15 Y-15 | 2-16 Y-16 | 2-17 Y-17 | 2-18 Y-18 | 2-19 Y-19 | 2-20 Y-20 | 2-21 Y-21 |
| Cosmetic composition No. |  |  |  |  |  |  |  |  |  |  |  |  |
| Composition (parts) | Solvent A | Ethanol | 74 | 74 | 74 | 74 | 74 | 74 | 74 | 74 | 74 | 74 |
|  | Solvent B | PARLEAM 3 | 20 | 20 | 20 | 20 | 20 | 20 | 20 | 20 | 20 | 20 |
|  | Polymer C | Anionic polymer CI | ULTRAHOLD 8 | 3 |  |  |  |  |  | 3 | 3 | 3 |  |
|  |  |  | ULTRAHOLD STRONG | 3 |  |  |  |  | 3 |  |  |  |  |
|  |  |  | ULTRAHOLD POWER |  | 3 |  |  |  | 3 |  |  |  | 3 |
|  |  | Cationic polymer CII-1 | Cationic polymer 1 |  |  | 3 |  |  |  |  | 3 |  |  |
|  |  |  | Cationic polymer 2 |  |  |  | 3 |  |  |  |  |  |  |
|  |  | Cationic silicone polymer CII-2 | Cationic silicone polymer 1 |  |  |  |  |  |  |  |  | 3 |  |
|  |  |  | Cationic silicone polymer 2 |  |  |  |  |  |  |  |  |  | 3 |
|  |  |  | Cationic silicone polymer 3 |  |  |  |  | 3 |  |  | 3 |  |  |
|  |  | Betaine polymer CIII | YUKA FORMER SM-dry |  |  |  |  |  |  |  |  |  |  |
|  |  | Nonionic polymer | Polyvinyl butyral |  |  |  |  |  |  |  |  |  |  |
|  |  |  | Polyurethanepolyurea |  |  |  |  |  |  |  |  |  |  |
| Viscosity of cosmetic composition (mPa·s) |  |  | 3.8 | 5.2 | 22.3 | 7.0 | 2.9 | 6.6 | 9.1 | 3.6 | 4.1 | 7.8 |
| Evaluation | Cosmetic coating film No. |  | 2-12 | 2-13 | 2-14 | 2-15 | 2-16 | 2-17 | 2-18 | 2-19 | 2-20 | 2-21 |
|  | Whiteness (image density) |  | 0.81 | 0.81 | 0.94 | 0.77 | 0.64 | 0.70 | 0.80 | 0.79 | 0.78 | 0.55 |

|  |  |  | Example |  |  |  |  |  |  |  |  |
|---|---|---|---|---|---|---|---|---|---|---|---|
|  |  |  | 2-22 Y-22 | 2-23 Y-23 | 2-24 Y-24 | 2-25 Y-25 | 2-26 Y-26 | 2-27 Y-27 | 2-28 Y-28 | 2-29 Y-29 | 2-30 Y-30 |
| Cosmetic composition No. |  |  |  |  |  |  |  |  |  |  |  |
| Composition (parts) | Solvent A | Ethanol | 74 | 74 | 74 | 74 | 74 | 74 | 74 | 74 | 74 |
|  | Solvent B | PARLEAM 3 | 20 | 20 | 20 | 20 | 20 | 20 | 20 | 20 | 20 |
|  | Polymer C | Anionic polymer CI | ULTRAHOLD 8 |  |  |  |  |  |  |  | 2 |  |
|  |  |  | ULTRAHOLD STRONG |  |  |  |  |  |  |  |  |  |
|  |  |  | ULTRAHOLD POWER | 3 |  |  |  |  |  |  |  |  |
|  |  | Cationic polymer CII-1 | Cationic polymer 1 |  | 3 | 3 |  |  |  |  |  |  |
|  |  |  | Cationic polymer 2 |  |  |  | 3 | 3 | 3 |  |  |  |
|  |  | Cationic silicone polymer CII-2 | Cationic silicone polymer 1 |  |  |  | 3 |  |  |  |  |  |
|  |  |  | Cationic silicone polymer 2 |  | 3 |  |  | 3 |  |  |  |  |
|  |  |  | Cationic silicone polymer 3 | 3 |  | 3 |  |  | 3 | 2 |  |  |
|  |  | Betaine polymer CIII | YUKA FORMER SM-dry |  |  |  |  |  |  | 2 |  |  |
|  |  | Nonionic polymer | Polyvinyl butyral |  |  |  |  |  |  |  | 6 |  |
|  |  |  | Polyurethanepolyurea |  |  |  |  |  |  |  |  | 6 |
| Viscosity of cosmetic composition (mPa·s) |  |  | 5.4 | 6.9 | 5.1 | 5.7 | 7.8 | 5.5 | 6.5 | 25.3 | 4.8 |
| Evaluation | Cosmetic coating film No. |  | 2-22 | 2-23 | 2-24 | 2-25 | 2-26 | 2-27 | 2-28 | 2-29 | 2-30 |
|  | Whiteness (image density) |  | 0.78 | 0.85 | 0.62 | 0.76 | 0.77 | 0.60 | 0.66 | 0.98 | 0.95 |

From Table 3, in Examples 2-1 to 2-6, in the case of single use of one kind of the polymer C, the betaine polymer CIII exhibited a high whiteness and excellent concealment, as compared with the anionic polymer CI and the cationic polymer CII-1.

In addition, from Table 3 and Table 4, in Examples 2-7 to 2-27, with respect to each of the anionic polymer CI and the cationic silicone polymer CII-2, in the case of joint use with the cationic silicone polymer CII-2, the whiteness was high, and the concealment was excellent, as compared with the single use thereof. Furthermore, with respect to the betaine polymer CIII, in the case of joint use with the anionic polymer CI or the cationic polymer CII-1, the whiteness was high, and the concealment was excellent, as compared with the single use thereof.

From Table 4, in Example 2-28, though the three kinds of the betaine polymer CIII, the anionic polymer CI, and the cationic silicone polymer CII-2 were used, the whiteness was high, and the concealment was excellent, as compared with single use of each of the anionic polymer CI and the cationic silicone polymer CII-2.

On the other hand, from Table 4, in Examples 2-29 and 2-30 using the nonionic polymer, though the whiteness was inferior to that in the case of using the ionic polymer, practically sufficient concealment was exhibited.

Examples 3-1 to 3-10

(Production of Cosmetic Composition)

The polymer C described in Table 5 was dissolved in absolute ethanol as the solvent A; after confirming that the solution was transparent and free from a floating material and a precipitate, the solvent B described in Table 5 was added; the contents were stirred and homogenized; and the resultant was filtered with a cellulose acetate syringe filter having a pore diameter of 0.20 μm, manufactured by Advantech Co., Ltd. There were thus obtained cosmetic compositions Z-1 to Z-10.

The dissolved amount of each of the polymers C used in Examples 3-1 to 3-10 in 100 g of the solvent B was less than 5 g, and the dissolved amount thereof in 100 g of the solvent A was 5 g or more.

(Preparation of Cosmetic Coating Film and Evaluation of Whiteness Expression Speed and Whiteness)

Cosmetic coating films 3-1 to 3-10 were prepared and evaluated for the whiteness in the same manners as mentioned above.

In the evaluation of the whiteness, after coating, the whiteness was measured every 5 minutes, and a time necessary until the value of whiteness became stable was measured, thereby evaluating the whiteness expression speed. On the occasion of measuring the whiteness, at the point of time when a difference from the whiteness measured 5 minutes ago became 0.1 or less was considered such that the whiteness became stable, and that time was recorded, whereby the whiteness on that occasion was evaluated. The results are shown in Table 5.

As the time until the whiteness becomes stable is shorter, such is more preferred. The case where the time is 30 minutes or shorter is not practically problematic.

TABLE 5

| | | | | | | | Example | | | | | | | |
|---|---|---|---|---|---|---|---|---|---|---|---|---|---|---|
| | | | | | 3-1 | 3-2 | 3-3 | 3-4 | 3-5 | 3-6 | 3-7 | 3-8 | 3-9 | 3-10 |
| | | | | | Z-1 | Z-2 | Z-3 | Z-4 | Z-5 | Z-6 | Z-7 | Z-8 | Z-9 | Z-10 |
| Cosmetic composition No. | | | | | | | | | | | | | | |
| Composition (parts) | Solvent A | Ethanol (boiling point: 78° C., Ra: 24) | | | 88 | 86 | 84 | 79 | 74 | 69 | 64 | 74 | 88 | 88 |
| | Solvent B | Kind | Boiling point (° C.) | Pa | | | | | | | | | | |
| | | PARLEAM 3 | 179 | 45 | 6 | 8 | 10 | 15 | 20 | 25 | 30 | | | |
| | | PARLEAM 4 | 262 | 45 | | | | | | | | 20 | | |
| | | KF-96A-1CS | 153 | 45 | | | | | | | | | 6 | |
| | | TMF-1.5 | 191 | 45 | | | | | | | | | | 6 |
| | Polymer C | ULTRAHOLD 8 | | | 3 | 3 | 3 | 3 | 3 | 3 | 3 | 3 | 2 | 2 |
| | | Cationic silicone polymer 3 | | | | | | | | | | | 2 | 2 |
| | | YUKA FORMER SM-dry | | | 3 | 3 | 3 | 3 | 3 | 3 | 3 | 3 | 2 | 2 |
| Viscosity of cosmetic composition (mPa · s) | | | | | 12.0 | 12.1 | 12.2 | 12.9 | 13.1 | 13.9 | 14.4 | 16.0 | 12.0 | 14.0 |
| Evaluation | | Cosmetic coating film No. | | | 3-1 | 3-2 | 3-3 | 3-4 | 3-5 | 3-6 | 3-7 | 3-8 | 3-9 | 3-10 |
| | | Whiteness expression speed [Time until the whiteness becomes stable (min)] | | | 10 | 15 | 15 | 15 | 20 | 20 | 20 | 20 | 10 | 10 |
| | | Whiteness (image density) | | | 0.66 | 0.51 | 0.41 | 0.38 | 0.26 | 0.37 | 0.41 | 0.27 | 0.75 | 0.81 |

From Table 5, Examples 3-1 to 3-10 quickly expressed a high whiteness and exhibited high concealment even without containing an inorganic pigment.

INDUSTRIAL APPLICABILITY

In accordance with the cosmetic composition of the present invention, a cosmetic composition for skin which is excellent in the concealment even without using an inorganic pigment can be provided.

The invention claimed is:
1. A cosmetic composition for skin comprising a solvent A, a solvent B, and a polymer C, wherein
a boiling point of the solvent A is lower than 99° C., and a distance Ra of the Hansen solubility parameter of the solvent A to water as expressed by the following equation (1) is 36 or less, a boiling point of the solvent B is 150° C. or higher, and
a distance Ra of the Hansen solubility parameter of the
solvent B to water as expressed by the following
equation (1) is 40 or more, the solvent B is compatible with the solvent A, the polymer C is soluble in the solvent A but insoluble in the solvent B, a content of the solvent A in the cosmetic composition is 50% by mass or more and 90% by mass or less, a content of the solvent B in the cosmetic composition is 5% by mass or more and 40% by mass or less, and a content of the polymer C in the cosmetic composition is 2% by mass or more and 15% by mass or less:

$$Ra=(4\times\Delta D^2+\Delta P^2+\Delta H^2)^{0.5} \quad (1)$$

wherein,

ΔD is a difference of dispersing component in the Hansen solubility parameter between a solvent and water, ΔP is a difference of a polar component in the Hansen solubility parameter between a solvent and water, and ΔH is a difference of hydrogen-binding component in the Hansen solubility parameter between a solvent and water.

2. The cosmetic composition for skin according to claim 1, wherein the solvent A is at least one selected from the group consisting of ethanol, propanol, isopropanol, and tert-butyl alcohol.

3. The cosmetic composition for skin according to claim 1, wherein the solvent B comprises 50% by mass or more of at least one selected from the group consisting of a hydrocarbon oil and a silicone oil each having a weight average molecular weight of 150 or more and 1,000 or less.

4. The cosmetic composition for skin according to claim 1, wherein the polymer C comprises, as a constitutional unit, at least one selected from the group consisting of a monomer having an acidic group, a monomer having a basic group, and a betaine monomer.

5. The cosmetic composition for skin according to claim 1, to wherein the polymer C comprises an anionic polymer CI comprising a constitutional unit derived from a monomer having an acidic group; and at least one selected from the group consisting of a cationic polymer CH-1 comprising a constitutional unit derived from a monomer having a basic group, a cationic silicone polymer CII-2, and a betaine polymer CIII comprising a constitutional unit derived from a betaine monomer.

6. The cosmetic composition for skin according to claim 1, wherein the polymer C comprises an anionic polymer CI comprising a constitutional unit derived from a monomer having an acidic group; and a betaine polymer CIII comprising a constitutional unit derived from a betaine monomer.

7. The cosmetic composition for skin according to claim 4, wherein the betaine monomer is at least one selected from the group consisting of a carboxybetaine monomer, a sulfobetaine monomer, and a phosphobetaine monomer.

8. The cosmetic composition for skin according to claim 1, which has a viscosity at 20° C. of 1 mPa·s or more and 300 mPa·s or less.

9. A cosmetic coating film for skin, comprising the cosmetic composition for skin according to claim 1.

10. The cosmetic composition for skin according to claim 3, wherein the hydrocarbon oil is at least one selected from the group consisting of ct-olefin oligomers, liquid paraffins, liquid isoparaffins, heavy liquid isoparaffins, liquid ozokerite, squalane, pristane, and squalene.

11. The cosmetic composition for skin according to claim 3, wherein the silicone oil is at least one selected from the group consisting of linear silicone oils, branched silicone oils, and cyclic silicone oils.

12. The cosmetic composition for skin according to claim 1, wherein a mass ratio of the content of the solvent A to that of the solvent B in the cosmetic composition is 0.01 or more and 50 or less.

13. The cosmetic composition for skin according to claim 1, wherein a mass ratio of the content of the polymer C to a total content of the solvent A and the solvent B in the cosmetic composition is 0.01 or more and 1 or less.

14. The cosmetic composition for skin according to claim 5, wherein the anionic polymer CI is a copolymer comprising a constitutional unit derived from the monomer having an acidic group and a constitutional unit derived from a monomer other than the monomer having an acidic group.

15. The cosmetic composition for skin according to claim 5, wherein the cationic polymer CII-1 is a copolymer of a monomer having a basic group and a monomer other than the monomer having a basic group.

16. The cosmetic composition for skin according to claim 5, wherein the cationic silicone polymer CII-2 is a poly(N-acylalkyleneimine)/organopolysiloxane copolymer comprising an organopolysiloxane segment (x) and a poly(N-acylalkyleneimine) segment (y) composed of an alkylene group comprising a cationic nitrogen atom binding to at least one silicon atom of the segment (x) and a repeating unit of an N-acylalkyleneimine.

17. The cosmetic composition for skin according to claim 5, wherein the betaine polymer CIII is at least one selected from the group consisting of polymethacryloylethyl dimethylbetaine, an N-methacryloyloxyethyl-N,N-dimethylammonium-a-N-methylcarboxybetaine/methacrylic acid alkyl ester copolymer, a methacryloylethyldimethylbetaine/methacryloylethyltrimethylammonium chloride/2-hydroxyethyl methacrylate copolymer, and a methacryloylethyldimethylbetaine/methacryloyethyltrimethylammonium chloride/methacrylic acid/methoxypolyethylene glycol copolymer.

18. The cosmetic composition for skin according to claim 5, wherein a total content of the anionic polymer CI, the cationic polymer CII-1, the cationic silicone polymer CII-2, and the betaine polymer CIII in the polymer C is 60% by mass or more and 100% by mass or less.

19. The cosmetic composition for skin according to claim 6, wherein a mass ratio of contents of the anionic polymer CI to the betaine polymer CIII is 0.1 or more and 9 or less.

20. The cosmetic composition for skin according to claim 1, wherein a content of an inorganic pigment in the cosmetic composition is 10% by mass or less.

* * * * *